United States Patent [19]

Rise

[11] Patent Number: 5,643,207

[45] Date of Patent: Jul. 1, 1997

[54] IMPLANTABLE TECHNIQUES FOR INFUSING A THERAPEUTIC AGENT WITH ENDOGENOUS BODILY FLUID

[75] Inventor: Mark T. Rise, Monticello, Minn.

[73] Assignee: Medtronic, Inc., Minneapolis, Minn.

[21] Appl. No.: 670,297

[22] Filed: Jun. 27, 1996

Related U.S. Application Data

[63] Continuation of Ser. No. 430,981, Apr. 28, 1995, abandoned.

[51] Int. Cl.$^6$ ................................................ A61M 11/00
[52] U.S. Cl. ................. 604/93; 604/891.1; 604/65; 604/67; 604/246
[58] Field of Search ............. 604/93, 19, 891.1, 604/48, 50, 65, 66, 67, 245, 246; 120/DIG. 12

[56] References Cited

U.S. PATENT DOCUMENTS

| | | | |
|---|---|---|---|
| 4,692,147 | 9/1987 | Duggan | 604/891.1 |
| 4,978,338 | 12/1990 | Melsky et al. | 604/93 |
| 5,073,094 | 12/1991 | Dorman et al. | 604/9 |
| 5,109,850 | 5/1992 | Blanco et al. | 604/50 |
| 5,316,053 | 5/1994 | Waber | 141/1 |

FOREIGN PATENT DOCUMENTS

| | | |
|---|---|---|
| 9325816 | 12/1993 | WIPO . |
| 9404257 | 3/1994 | WIPO . |

OTHER PUBLICATIONS

Siemens AG, "Device for Infusing a Medical Liquid Adapted for Implantation in a Human or Animal Body", Opp Pub. Date: Dec. 29, 1983, Pub No. 27 21 752 Germany.

*Primary Examiner*—Michael Powell Buiz
*Assistant Examiner*—N. Kent Gring
*Attorney, Agent, or Firm*—Curtis D. Kinghorn; Harold R. Patton

[57] ABSTRACT

An implantable system for infusing an agent into an organ containing an endogenous fluid, including an implantable reservoir for the agent and implantable first and second catheters implanted in the organ. An implantable pump transmits the endogenous fluid to the organ through one catheter and returns it through the other catheter. A predetermined quantity of the agent is added from the reservoir to the endogenous fluid to facilitate buffering and dilution of the agent before administration to the organ.

33 Claims, 5 Drawing Sheets

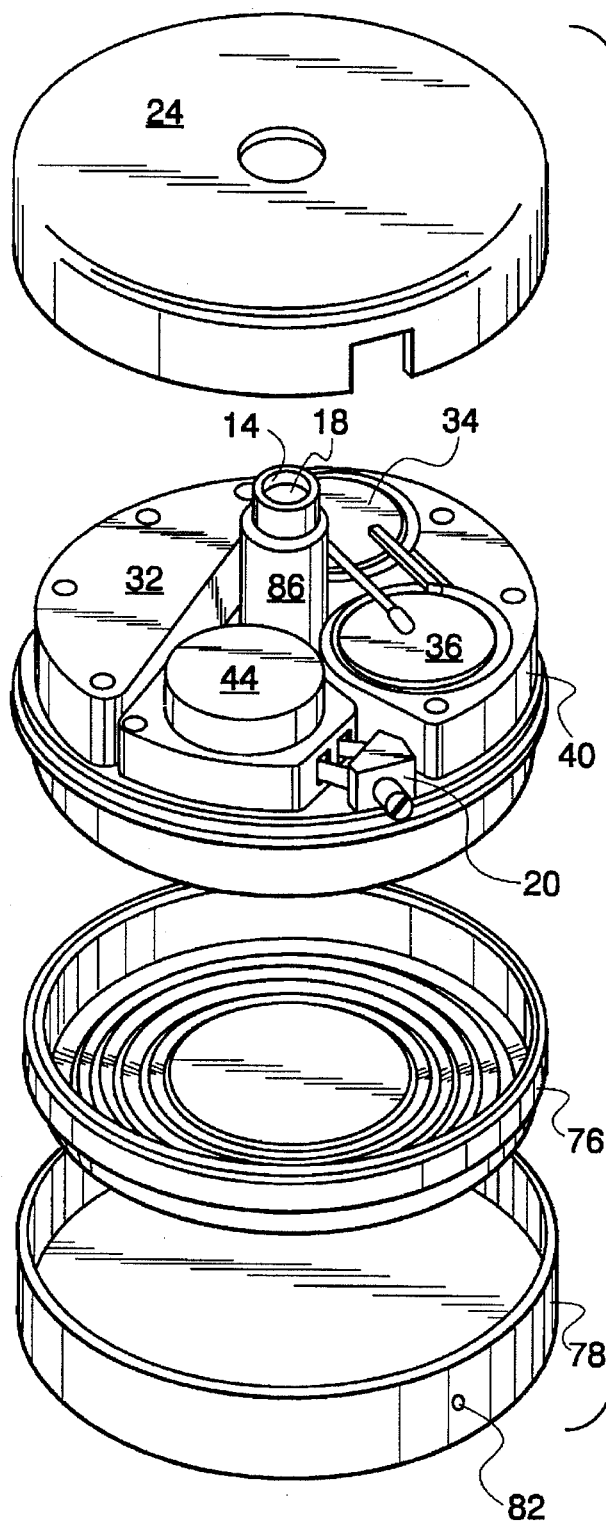
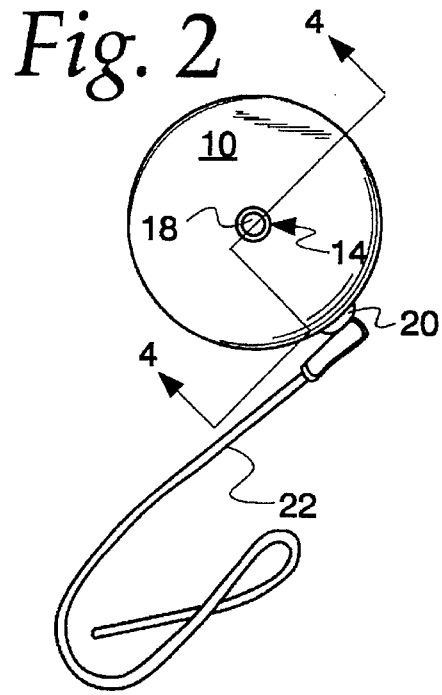
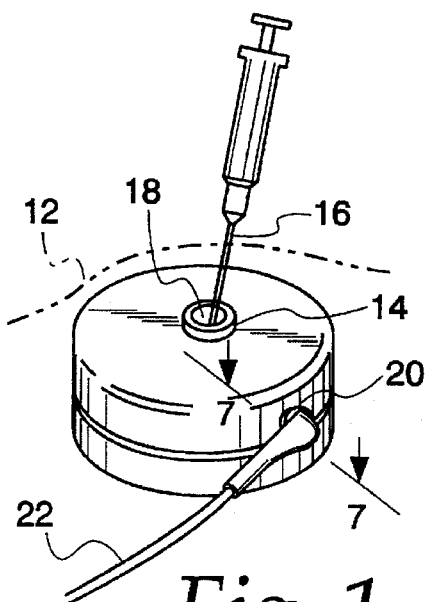
Fig. 2
Fig. 3
Fig. 1

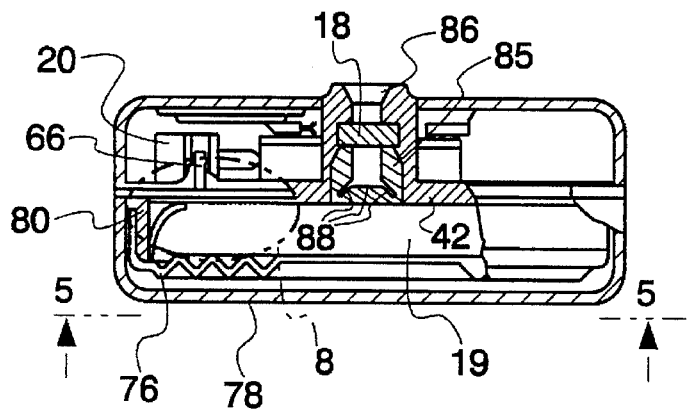
*Fig. 4*   *Fig. 5*
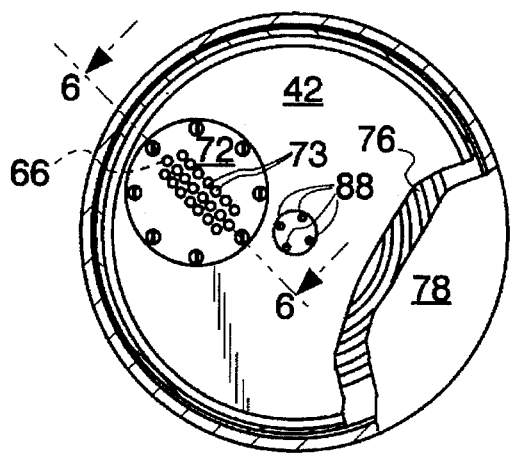
*Fig. 6*
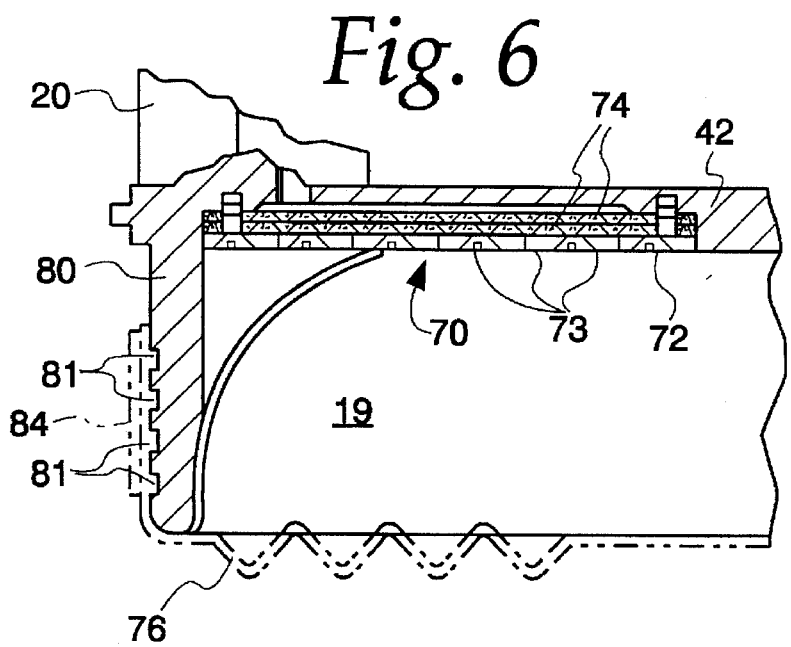

5,643,207

IMPLANTABLE TECHNIQUES FOR INFUSING A THERAPEUTIC AGENT WITH ENDOGENOUS BODILY FLUID

This application is a continuation of application Ser. No. 08/430,981 filed on Apr. 28, 1995, abandoned.

BACKGROUND OF THE INVENTION

1. Field of the Invention

This invention relates to implantable techniques for infusing a therapeutic agent into an organism and more particularly relates to such techniques for delivering such a therapeutic agent with a patient's own endogenous fluid.

2. Description of the Related Art

When chronic administration of a pharmaceutically active agent is required, internal delivery by an implantable infusion pump ("IIP"), in combination with a catheter, may be the desired delivery means. For example, IIP-catheter delivery may be preferred when the site specific delivery of the agent is critical, or the agent must be administered to spaced sites in tightly controlled, yet minute dosages.

Experience has shown for minute dosages, the therapeutic agent may require buffering or dilution before being administered to the body, particularly if the parenchyma of the brain is the target organ. Certain proteins may need to be formulated at a pH different from the neutral pH optimal for safe delivery to the brain parenchyma. For example, a drug agent may need to be stored at an acidic or basic pH to achieve stability at body temperature, but it may need to be delivered into the brain parenchyma at or near neutral pH.

Experience has shown that the catheters used to administer the agent may require continuous or near continuous flow, even if therapeutic agent infusion is intermittent, in order to prevent clogging. However, it is difficult to provide continuous flow of relatively large volumes of fluid from an implanted pump, because the reservoir in such pumps necessarily has limited volume. The present invention is directed to solving the foregoing problems.

SUMMARY OF THE INVENTION

The invention is useful in implantable techniques for infusing an agent into an organ using an endogenous fluid. An implantable reservoir is used to hold a quantity of the agent. First and second implantable catheters suitable for implantation into the organ are also provided. The endogenous fluid is transmitted through the first catheter and is transmitted to the organ through the second catheter. A predetermined quantity of the agent from the reservoir is added to at least a portion of the transmitted endogenous fluid.

By using the foregoing techniques, the patency of the first and second catheters is facilitated by flow of the endogenous fluid through the first and second catheters. The addition of the agent to the endogenous fluid facilitates buffering and facilities dilution of the agent before administration to the organ. By using the foregoing techniques, minute quantities of agents may be administered to organs with a degree of safety and efficacy previously unattained by the prior art.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 1 is a diagrammatic view of a preferred form of device made in accordance with the present invention implanted beneath skin (shown in phantom) with a reservoir of the device being filled by a hypodermic syringe;

FIG. 2 is a plan view of the device shown in FIG. 1;

FIG. 3 is an exploded view of the device shown in FIG. 1 with the catheter removed;

FIG. 4 is a cross sectional view of the device taken along line 4—4 of FIG. 2 to reveal the reservoir;

FIG. 5 is a cutaway bottom plan view of the device with portions cutaway to reveal the reservoir and associated elements;

FIG. 6 is a cross sectional view of a filter of the device taken along line 6—6 of FIG. 5 and a detail of FIG. 4 taken at 8 and shown in enlarged scale;

DESCRIPTION OF THE PREFERRED EMBODIMENTS

Figure 7:
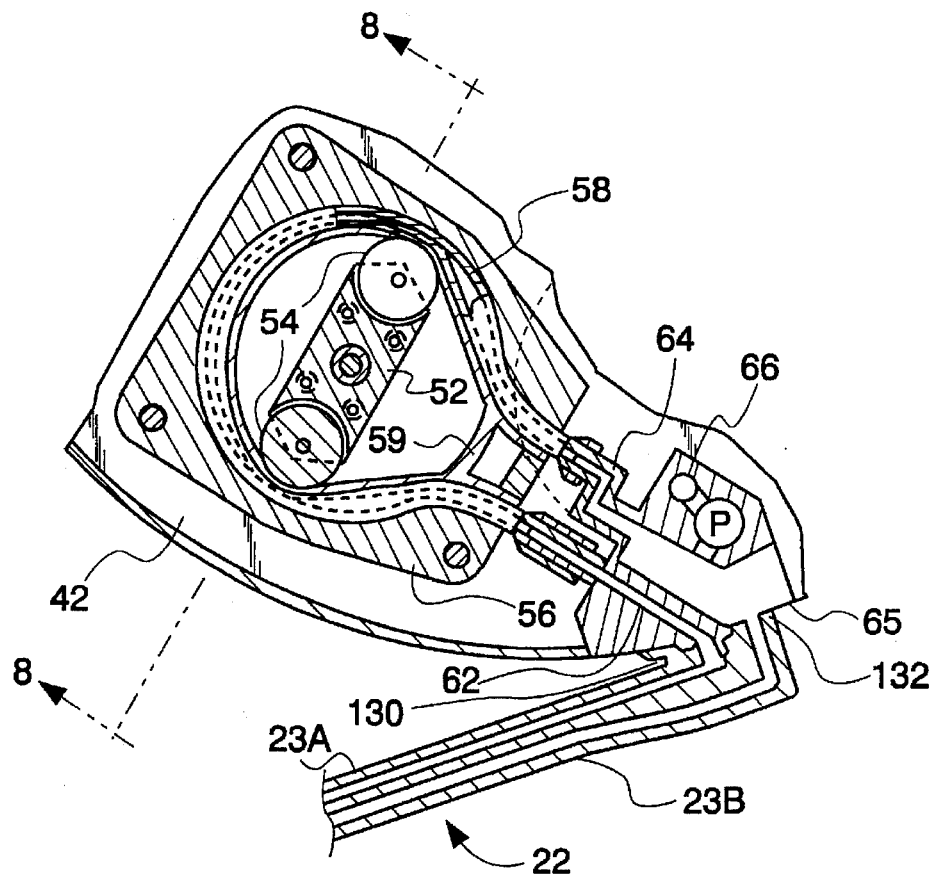
FIG. 7 is a cross sectional view of a pump/meter of the device taken along line 7—7 of FIG. 1.

Referring to FIGS. 1 and 2, an administration system or device 10 made in accordance with the preferred embodiment is shown implanted below a layer of skin 12 indicated in phantom. The administration device has a port 14 into which a hypodermic needle 16 can be inserted through the skin 12 to insert a quantity of a liquid agent, such as a medication, a growth factor, an antisense agent, an ionic solution, one or more antibodies, a hormone, proteins or peptides, viruses, cell suspension, a chemotherapeutic agent or toxin, or some drug, through a septum 18 into a drug reservoir 19 (FIG. 4) located within drug administration device 10. The liquid agent is delivered from device 10 through a catheter port 20 to which a catheter 22 is attached. The catheter 22 is positioned to deliver the agent to spaced infusion sites.

Referring to FIG. 3, a circuit module 32 is driven by suitable batteries 34 and 36 which are connected to battery input terminals of an electronic module 32.

Figure 8:
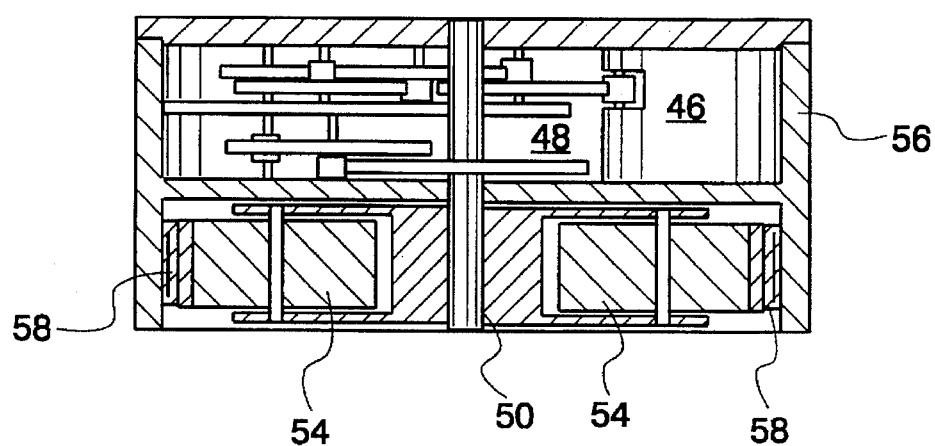
FIG. 8 is a cross sectional view of the pump taken along line 8—8 of FIG. 7 and a schematic illustration of a second pump.

A peristaltic roller pump 44 is shown in more detail in FIGS. 7 and 8. A motor 46 drives a gear train 48, which in turn drives a shaft 50 that is connected to an arm 52. Motor 42 is a two pole subminiature stepping motor of the type used in digital watches having analog time indicating means. Such motors are manufactured by Seiko Corporation. The winding of motor 42 is driven by electrical pulses from electronics module 32 which step the motor through a fixed arc for each pulse.

Rollers 54 are each mounted for rotation about their axes at both ends of arm 52 which is rotatable through 360°. As shaft 50 is rotated, arm 52 and rollers 54 are rotated about the axis of shaft 50. The arm is located within a housing 56 and a flexible tube 58 lines the interior wall of housing 56 as shown in FIG. 7. A shim 59 is interposed between rollers 54 and tubing 58 to aid in balancing the forces applied to shaft 50 as rollers 54 traverse a complete revolution of shaft 50. As shaft 50 rotates, the wheels 54 roll along shim 59 and compress tubing 58 against the inner wall of housing 56.

Pump 44 is connected to catheter port 20 which provides an outlet conduit 62 that is connected to tube 23A of catheter 22 screwed onto port 20. Pump 44 receives its input from an inlet conduit 64 which is connected to a mixing chamber 65. Chamber 65 receives endogenous fluid from tube 23B of catheter 22 and receives therapeutic agent from reservoir 19 through an inlet port 66 by means of a pump P that is started and stopped by signals transmitted over conductors (not shown) from module 32. Pump P preferably is a micropump fabricated by micromachining. Exemplary pumps are described by B. T. G. van Lintel et al. in "A Piezoelectric Micropump Based on Micromachining of Silicon," 15 *Sensors and Actuators* 153–163 (1988) and by Jan G. Smits in "Piezoelectric Micropump with Three Valves Working Peristaltically," A21–A23 *Sensors and Actuators* 203–206 (1990). As shown in FIG. 7, tube 23A has a proximal end 130 and tube 23B has a proximal end 132. Proximal end 130 of tube 23A is coupled to chamber 65 through tube 58 of pump 44.

Inlet port 66 communicates with fluid reservoir 19 through a filter 70 shown in FIG. 5 and in cross section in FIGS. 4 and 6. As shown in FIG. 6, filter 70 comprises a clamping ring and screen 72 which has a number of holes 73 for permitting the flow of a liquid through the filter. The clamp ring and screen 72 holds a pair of fine filters 74 for screening out any particles of skin or hair which could have reached fluid reservoir 19 when the reservoir is filled utilizing a hypodermic needle inserted through the patient's skin.

Reservoir 19 is formed with its top portion being the underside of housing 42 and its lower portion formed from a flexible diaphragm 76 that is protected by a lower shield 78 which forms a seal against a projecting flange 80. The flange has a plurality of circumferential sealing grooves 81 which project from housing 42. Upper shield portion 24 also is seated against flange 80. The diaphragm is secured to housing 42 with a circumferential Teflon band 84 and a suitable adhesive to form a sealed reservoir.

After sealed reservoir 19 has been formed and lower shield 78 has been positioned against flange 80 of housing 42, the space between diaphragm 76 and lower housing 78 is evacuated through hole 82 shown in FIG. 3, and a small amount of a suitable fluorocarbon liquid is inserted in the hole to backfill the device. Hole 82 is then welded to seal the unit. In one embodiment, approximately 2.5 CCs of Fluorinert FIC88 is inserted in the unit. The amount of fluorocarbon fluid, or other suitable volatile fluid, is selected to provide a positive pressure against bellows 76 when the administration device is implanted in the patient's body. As is well known in the art, such a volatile fluid exerts a constant vapor pressure at a given temperature regardless of volume. Thus, the constant positive pressure compresses bellows 76 and urges the liquid contents of the reservoir 19 through filter 70. The fluid is forced through screen 72 and filter segments 74 to input port 66 of pump 56. As pump 44 rotates, the rolling action of rollers 54 at the ends of arm 52 allows a predetermined amount of liquid to be either pumped or metered from reservoir 19 through catheter 22 to the location within the body where it is desired to apply the fluid agent.

The fluid supply in the reservoir is periodically replenished by applying a hypodermic needle 16 as shown in FIG. 1. The hypodermic needle pierces the septum 18. As shown in FIG. 4, the septum 18 is seated against a plug 85. Plug 85 and septum 18 are mounted in a projecting neck portion 86 of housing 42. Neck portion 86 has a central opening to permit access to septum 18 by hypodermic needle 16.

Needle 16 is forced through the septum 18 which may be formed of a silicone rubber compound. If the hypodermic needle 16 has a rounded blunt tip and a delivery port located on the shaft of the needle, the insertion of the needle through the septum 18 will not cause a permanent hole to form in septum 18. After the hypodermic needle has been forced through the septum, its contents are delivered into chamber in plug 85 under pressure when the pressure of its contents exceeds the pressure of reservoir 19, which is typically 3 to 5 psi. The fluid is forced into reservoir 19 through apertures 88 in plug 85, and bellows 76 is expanded to accept the fluid. The hypodermic needle is then withdrawn and the silicone rubber of septum 18 reseals.

Electronic module 32 can be identical to the like numbered module shown in U.S. Pat. No. 4,692,147 that is incorporated by reference. Programming command information may be applied as taught in the foregoing U.S. patent.

Figure 9:
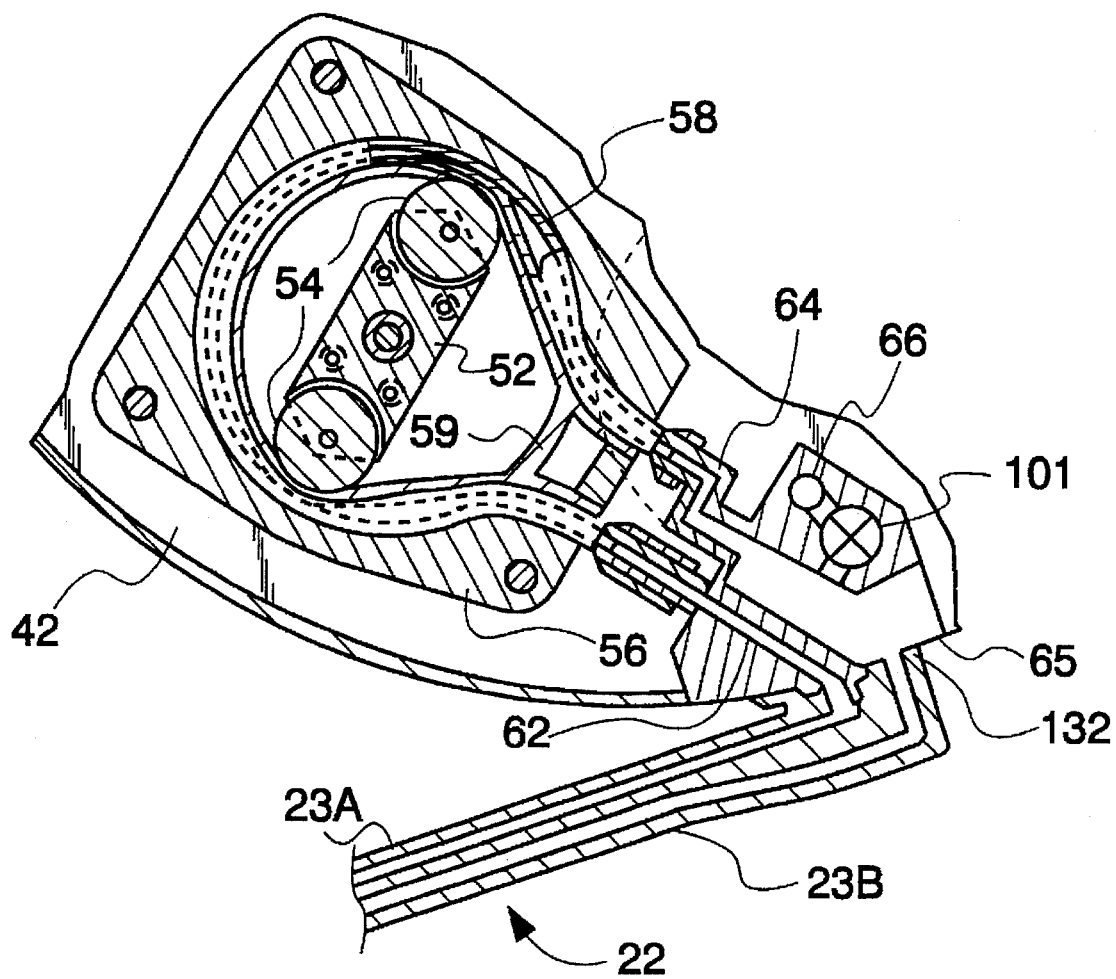
FIG. 9 is an alternative embodiment of the device shown in FIG. 7 in which the second pump is replaced with a valve.

Another embodiment of the device is shown in FIG. 9. In this embodiment, pump P is replaced by a valve 101 which is opened and closed by signals conducted from module 32 over conductors (not shown). An exemplary valve is described by T. Ohnstein et al. in "Micromachined Silicon Microvalve," Proceedings, IEEE, Micro Electro Mechanical Systems, Napa Valley, Calif., pages 95–98 (Feb. 11–14, 1990).

Figure 10:
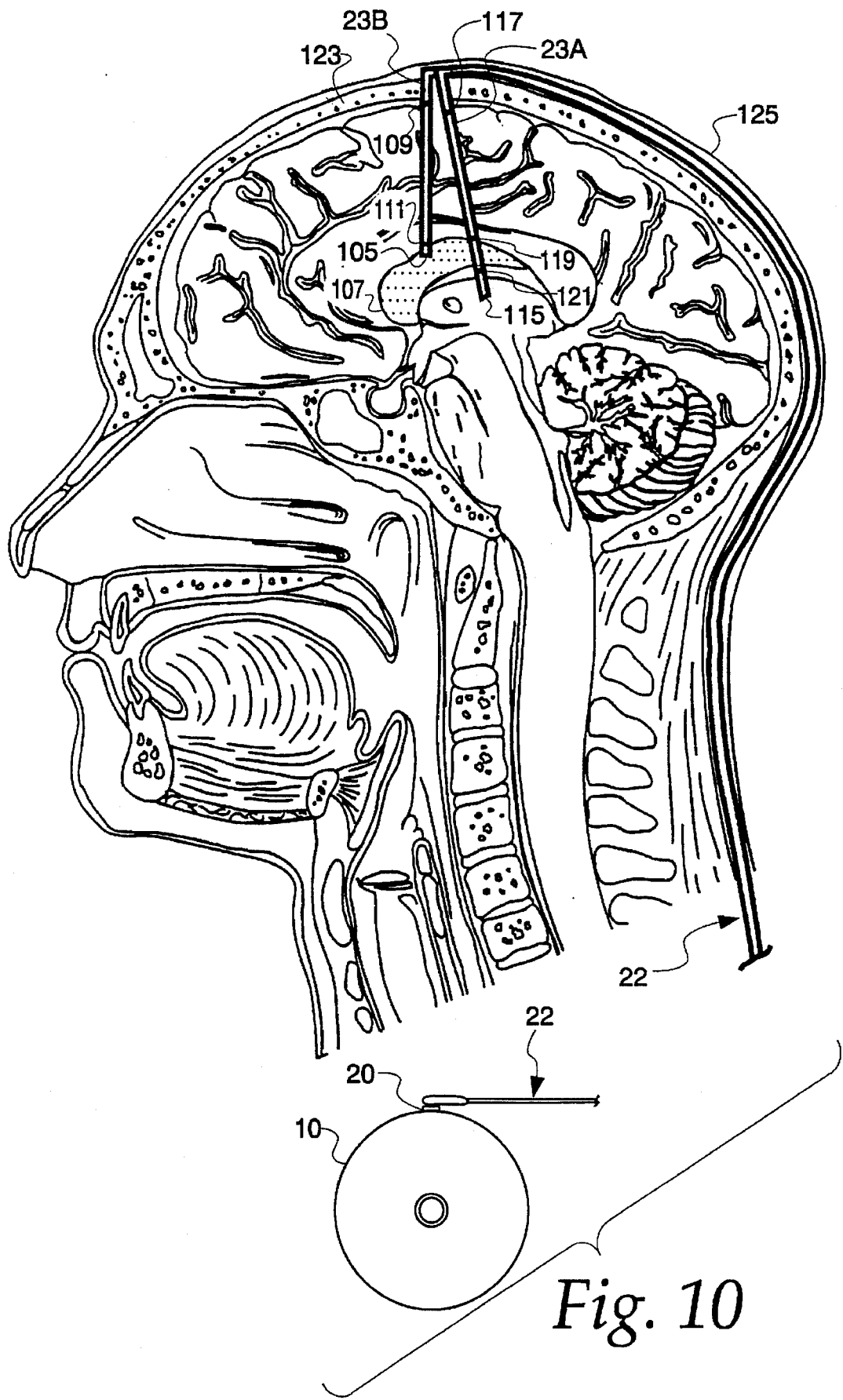
FIG. 10 is a diagrammatic illustration of the catheter implanted in a brain.

Referring to FIG. 10, tubes 23A and 23B of catheter 22 are implanted in the brain as shown by conventional stereotactic surgery techniques. Distal end 105 of tube 23B is implanted into a portion 107 of the lateral ventricle of the brain. The portion of tube 23B between lines 109 and 111 is located in the parenchyma of the brain.

Tube 23A has a distal end 115 implanted in the parenchyma of the brain. The portion of tube 23A between lines 117 and 119, as well as the portion between line 121 and distal end 115, are located in the parenchyma of the brain.

Tubes 23A and 23B are surgically implanted through a hole in the skull 123, and catheter 122 is implanted between the skull and the scalp 125 as shown in FIG. 10. Catheter 22 is joined to implanted device 10 in the manner shown.

In operation, cerebral spinal fluid is drawn through distal end 105 tube 23B and through catheter 22 into mixing chamber 65 (FIG. 7). The fluid is drawn through inlet conduit 64 and into tube 58 by the operation of rollers 54 and arm 52 of pump 44 which cause cerebral spinal fluid to pass through tube 58 and into tube 23A of catheter 32. The pressure from the pump causes the cerebral spinal fluid to flow through catheter 22 and into the parenchyma of the brain through tube 23A. Pump 44 is operated substantially continuously in order to improve the patency of catheter tubes 23A and 23B. The flow of cerebral spinal fluid through tubes 23A and 23B keeps their distal ends 105 and 115 opened and unclogged.

Alternatively, tube 23B can be implanted in the vascular system so that blood plasma is transmitted into chamber 65 and mixed with an agent. Pump 44 transmits the agent and blood plasma through tube 23A into the parenchyma of an organ, such as bone or the pancreas.

A therapeutic agent periodically is added to mixing chamber 65 by operation of pump P (FIG. 7). Pump P is operated by signals from electronic module 32. The pump transports a predetermined quantity of the agent from reservoir 19 through port 66 into mixing chamber 65. In chamber 65, the therapeutic agent is mixed with the cerebral spinal fluid. This is an important feature which buffers the agent and also dilutes the agent before administration to the brain through tube 23A. As a result, the therapeutic agent can be kept in reservoir 19 in either an acidic or a basic environment, which best preserves the efficacy of the agent.

Referring to FIG. 9, valve 101 may be substituted for pump P. In this embodiment, therapeutic agent is added from reservoir 19 to mixing chamber 65 by opening valve 101 for a predetermined time period. The signals from module 32 can be timed to add a predetermined quantity of the agent to mixing chamber 65. Since bellows 76 applies pressure to the therapeutic agent reservoir 19, the agent flows freely through valve 101 whenever it is opened.

Those skilled in the art will recognize that the preferred embodiments may be altered or amended without departing from the true spirit and scope of the invention, as defined in the accompanying claims.

I claim:

1. A method for infusing an agent into an organ of a human body using said body's own endogenous fluid, said method comprising he steps of:

holding a quantity of said agent inside said body;

collecting a portion of said endogenous fluid;

transmitting a portion of said collected endogenous fluid into said organ; and adding, within said body from said quantity of said agent, a predetermined dose of said agent to at least a portion of said endogenous fluid transmitted into said organ, whereby the addition of said agent to said endogenous fluid facilitates buffering and dilution of said agent before administration to said organ.

2. A method, as claimed in claim 1, wherein said organ is the brain and said endogenous fluid is cerebrospinal fluid.

3. A method, as claimed in claim 1, wherein said organ is the pancreas and said endogenous fluid is blood plasma.

4. A method, as claimed in claim 1, wherein said step of transferring comprises the step of pumping.

5. A method, as claimed in claim 1, wherein said step of transmitting is conducted substantially continuously.

6. A method, as claimed in claim 5, wherein said step of adding comprises the step of adding said agent periodically, so that said endogenous fluid is transmitted substantially continuously and said agent is transmitted to said organ periodically.

7. A method, as claimed in claim 1, wherein said step of adding comprises the step of mixing said dose of said agent with a predetermined quantity of said endogenous fluid, whereby control of the concentration of said agent in said endogenous fluid is facilitated.

8. A method, as claimed in claim 1, wherein said organ is the brain.

9. A method, as claimed in claim 1, wherein said endogenous fluid is cerebrospinal fluid.

10. A method, as claimed in claim 1, wherein said organ is the pancreas.

11. A method, as claimed in claim 1, wherein said endogenous fluid is blood plasma.

12. A method for infusing an agent into an organ in a body using an endogenous fluid comprising the steps of;

implanting a pump in said body;

fluidly connecting a reservoir to said pump, said reservoir holding a quantity of said agent;

implanting a first catheter in said body, said first catheter having a proximal end fluidly connected to said pump, said first catheter having a distal end implanted in said endogenous fluid;

implanting a second catheter in said body, said second catheter having a proximal end fluidly connected to said pump, said second catheter having a distal end implanted in said organ;

pumping said endogenous fluid through said first catheter from said distal end of said first catheter to said pump;

pumping said endogenous fluid from said pump to said organ through said second catheter; and adding a predetermined quantity of said agent from said reservoir to at least a portion of said endogenous fluid pumped from said pump to said organ.

13. The method of claim 12 further comprising the step of implanting said reservoir in said body.

14. A method, as claimed in claim 12, wherein said organ is the brain.

15. A method, as claimed in claim 12, wherein said endogenous fluid is cerebrospinal fluid.

16. A method, as claimed in claim 12, wherein said organ is the brain and said endogenous fluid is cerebrospinal fluid.

17. A method, as claimed in claim 12, wherein said organ is the pancreas.

18. A method, as claimed in claim 12, wherein said endogenous fluid is blood plasma.

19. A method, as claimed in claim 12, wherein said organ is the pancreas and said endogenous fluid is blood plasma.

20. An implantable system for infusing an agent into an organ using an endogenous fluid, said system comprising in combination:

an implantable pump;

an implantable reservoir for holding a quantity of said agent, said implantable reservoir in fluid communication with said implantable pump:

an implantable first catheter having a proximal end fluidly connected to said implantable pump, said first catheter having a distal end suitable for implantation in said endogenous fluid;

an implantable second catheter having a proximal end fluidly connected to said implantable pump, said second catheter having a distal end suitable for implantation in said organ;

wherein said implantable pump pumps said endogenous fluid through said first catheter of said distal end of said first catheter to said pump and then pumps said endogenous fluid from said pump to said organ through said second catheter; and means for adding a predetermined quantity of said agent from said reservoir to at least a portion of said endogenous fluid pumped from said pump to said organ, whereby patency of said first and second catheters is facilitated by flow of said endogenous fluid through said first and second catheters and whereby the addition of said agent to said endogenous fluid facilitates buffering and dilution of said agent before administration to said organ.

21. A system, as claimed in claim 20, wherein said organ is the brain and said endogenous fluid is cerebrospinal fluid.

22. A system, as claimed in claim 20, wherein said organ is the pancreas and said endogenous fluid is blood plasma.

23. A system, as claimed in claim 20, wherein said pump operates substantially continuously.

24. A system, as claimed in claim 23, wherein said means for adding periodically adds said predetermined quantity of said agent to said endogenous fluid, so that said endogenous fluid is substantially continuously delivered to said organ and said agent is periodically delivered to said organ.

25. A system, as claimed in claim 20, wherein said pump includes a chamber for holding a predetermined quantity of said endogenous fluid, wherein said endogenous fluid flows from said first catheter into said chamber, wherein said means for adding transfers said agent from said reservoir to said chamber and wherein said second catheter transfers fluid from said chamber to said organ.

26. A system, as claimed in claim 25, wherein said means for adding comprises a second pump.

27. A system, as claimed in claim 26, wherein said second pump comprises a micromachined pump.

28. A system, as claimed in claim 20, wherein said pump comprises a peristaltic pump.

29. A system, as in claim 20, wherein said means for adding includes a valve controlling the addition of said agent to said endogenous fluid.

30. A system, as claimed in claim 20, wherein said organ is the brain.

31. A system, as claimed in claim 20, wherein said endogenous fluid is cerebrospinal fluid.

32. A system, as claimed in claim 20, wherein said organ is the pancreas.

33. A system, as claimed in claim 20, wherein said endogenous fluid is blood plasma.

* * * * *

UNITED STATES PATENT AND TRADEMARK OFFICE
CERTIFICATE OF CORRECTION

PATENT NO. : 5,643,207
DATED : July 1, 1997
INVENTOR(S) : Mark T. Rise

It is certified that error appears in the above-identified patent and that said Letters Patent is hereby corrected as shown below:

Col. 6, Line 31    "pump:" should be " pump;"

Col. 5, Line 19    "he" should be "the"

Col. 5, Line 58    "of;" should be "of:"

Signed and Sealed this

Twenty-second Day of September, 1998

Attest:

BRUCE LEHMAN

Attesting Officer        Commissioner of Patents and Trademarks